United States Patent
Galarza

(12) 
(10) Patent No.: US 6,658,896 B2
(45) Date of Patent: Dec. 9, 2003

(54) METHOD OF MAKING A FIBEROPTIC LIGHT GUIDE

(75) Inventor: Antonio Galarza, Jacksonville, FL (US)

(73) Assignee: Sunoptic Technologies LLC, Jacksonville, FL (US)

( * ) Notice: Subject to any disclaimer, the term of this patent is extended or adjusted under 35 U.S.C. 154(b) by 150 days.

(21) Appl. No.: 10/052,196

(22) Filed: Jan. 18, 2002

(65) Prior Publication Data

US 2003/0138753 A1 Jul. 24, 2003

(51) Int. Cl.⁷ .............................................. C03B 37/028
(52) U.S. Cl. ............................... 65/408; 65/409; 65/411
(58) Field of Search ........................... 65/409, 411, 408

(56) References Cited

U.S. PATENT DOCUMENTS

| | | | | |
|---|---|---|---|---|
| 2,608,722 A | * | 9/1952 | stuetzer | 29/592.1 |
| 2,945,958 A | | 7/1960 | Morris | 250/230 |
| 3,166,395 A | * | 1/1965 | hicks | 65/402 |
| 3,350,183 A | * | 10/1967 | siegmund | 65/411 |
| 3,395,006 A | * | 7/1968 | hopkins | 65/501 |
| 4,076,378 A | | 2/1978 | Cole | 385/115 |
| 4,332,439 A | | 6/1982 | Lubbers et al. | 385/121 |
| 4,688,884 A | | 8/1987 | Scifres et al. | 385/38 |
| 4,697,867 A | | 10/1987 | Blanc et al. | 385/43 |
| 4,723,825 A | | 2/1988 | Herold | 433/141 |
| 4,792,692 A | | 12/1988 | Herold et al. | 250/504 H |
| 4,836,782 A | | 6/1989 | Gonser | 433/229 |
| 4,846,546 A | | 7/1989 | Cuda | 385/116 |
| 5,371,826 A | | 12/1994 | Friedman | 385/115 |
| 5,412,749 A | | 5/1995 | Sayegh et al. | 385/115 |
| 5,495,541 A | | 2/1996 | Murray et al. | 385/33 |
| 6,208,788 B1 | | 3/2001 | Nosov | 385/121 |
| 6,314,767 B2 | * | 11/2001 | Pezet et al. | 65/510 |

FOREIGN PATENT DOCUMENTS

| | | | | |
|---|---|---|---|---|
| DE | 2507601 A1 | | 1/1978 | |
| JP | 59-164522 | * | 9/1984 | 65/409 |

OTHER PUBLICATIONS

Cuda Products Corp., "Tapered Fused Rod", one page drawing, Jan. 1992.
Cuda Products Corp., "Tapered Probe", one page drawing, Nov. 1999.

* cited by examiner

Primary Examiner—John Hoffmann
(74) Attorney, Agent, or Firm—Howson and Howson

(57) ABSTRACT

A method of making a fiberoptic dental light probe having a bent distal end with a tapered tip. The method includes the step of heating just the mid-section of a vertically-disposed, solid, cylindrical fused fiberoptic rod and permitting the midsection to stretch and thin under its own weight by the force of gravity. Local heating of the mid-section is accomplished with a high-temperature small flame, such as the flame emitted by a gas-fired blow torch. The heat is removed when the rod stretches to a predetermined length, and then after the mid-section cools, the mid-section is cut to produce a pair of identical tapered tip probes. Thereafter, the distal ends of the probes can be bent to a desired angle and the ends of the probes can be cut to size, ground, and polished. A unique probe configuration is also provided.

16 Claims, 3 Drawing Sheets

METHOD OF MAKING A FIBEROPTIC LIGHT GUIDE

FIELD OF THE INVENTION

The present invention relates to light guides utilized, for instance, in curing resins in medical, dental, scientific, industrial and military applications. More particularly, the present invention relates to a method of making a fiberoptic light probe useful for producing a concentrated high-intensity light for curing a photocurable dental composition.

BACKGROUND OF THE INVENTION

Light guides are utilized to expose photocurable materials to high intensity visible light to change the materials from a paste-like putty to a substance having the hardness of ceramic or glass in a few seconds. Thus, for example, such probes have been utilized in dental procedures to harden photocurable sealants, adhesives and filler material for filling dental cavities. Of course, such a probe can be utilized in any application which requires an accurately directed high intensity light beam.

U.S. Pat. No. 4,846,546 issued to Joseph Cuda discloses a fiberoptic light guide useable as a dental probe. The elongate fiberoptic probe has a constant diameter from its proximal end to its distal end, and the distal end is angled at approximately 60° from the longitudinal axis of the proximal end of the probe so that a high intensity light beam can be accurately directed within a mouth of a patient during a dental procedure.

As disclosed in the above referenced Cuda patent, the probe is manufactured by inserting a bundle of closely packed elongate and continuous glass rod fibers into a hollow cylindrical glass cladding and then by drawing this assembly into a smaller diameter to create a heat-fused, solid, substantially-cylindrical fiberoptic rod. For example, as disclosed by the Cuda patent, hundreds of fibers can be inserted into a hollow cladding having a diameter of about 40 mm. The assembly can then be drawn to a diameter of about 8 mm throughout its length. The heat fused rod is then cut to length; a distal end of the rod is heated and bent to form a bent tip of the probe; and the ends of the probe are ground and polished. In addition, end fittings can be adhesively secured to the ends of the probe so that, for instance, the probe can be readily connected to a light gun or like high intensity light generating apparatus.

Another fiberoptic dental probe is disclosed in U.S. Pat. No. 5,371,826 issued to Friedman. The Friedman patent discloses a probe having a proximal end which tapers inwardly throughout its length to an angled distal end for purposes of concentrating the high intensity light.

Other light guides and probes are disclosed in German Published Patent Application No. DE 2507601 A1 and by U.S. Pat. Nos. 4,792,692 and 4,723,825 issued to Herold et al.; 4,836,782 issued to Gonser; 4,076,378 issued to Cole; 2,945,958 issued to Morris; 5,412,749 issued to Sayegh et al.; 5,495,541 issued to Murray et al.; 4,688,884 issued to Scifres et al.; 4,697,867 issued to Blanc et al.; 4,332,439 issued to Lübbers et al.; and 6,208,788 issued to Nosov.

While the aforementioned light guides and methods of their manufacture may be satisfactory for their intended purposes, there is a need for a fiberoptic probe having a tapered section which can be efficiently manufactured and which can be utilized to concentrate high intensity light. To this end, the method of making the probe should not require the complicated and expensive step of heating a fused fiberoptic rod along substantially its entire length within an expensive furnace apparatus to stretch the rod and provide the rod with a relatively long and continuous taper. Rather, the tapered section of the probe should be restricted to a relatively small section of the distal tip of the probe while the remaining sections of the probe remains at a substantially constant unmodified diameter throughout. In addition, preferably the probe made by the method should have a novel configuration which permits a concentrated high intensity light to be accurately directed within a mouth of a patient during a dental procedure.

OBJECTS OF THE INVENTION

With the foregoing in mind, a primary object of the present invention is to provide a method of making a fiberoptic light guide having a distal end with a relatively short-length tapered tip.

Another object of the present invention is to provide a method of efficiently stretching a fused fiberoptic rod without the need of an expensive furnace and heating element and complicated heating and stretching process.

A further object of the present invention is to provide a method of making a fiberoptic dental light probe which has a substantially constant diameter except for a relatively small section of an angled distal end of the probe.

A still further object of the present invention is to provide a dental fiberoptic dental light probe having a unique configuration which concentrates high intensity light and permits accurate direction of the light toward a photocurable resin within the mouth of a patient during a dental procedure.

SUMMARY OF THE INVENTION

More specifically, the present invention provides a method of making a fiberoptic light guide that includes the step of supporting in a vertically-disposed position an elongate fused fiberoptic rod having opposite ends and a mid-section located therebetween. Thereafter, only the mid-section of the elongate fused fiberoptic rod is heated to soften the mid-section such that the mid-section thins and elongates under its own weight by the force of gravity. The heating step is discontinued when the fused rod elongates to a predetermined length to prevent the mid-section from further stretching and to permit the mid-section to cool. After the mid-section cools, it is cut at the thinned and stretched area of the mid-section to provide a pair of separate, substantially-identical, fiberoptic light guides each having a tapered distal tip.

Preferably, the method is utilized to make a fiberoptic dental light probe and further includes the initial steps of inserting a bundle of optic fibers into a hollow cladding having a predetermined outer diameter, heating the cladding and optic fibers, and drawing the cladding and optic fibers to fuse the bundle of optic fibers together and to seal the bundle of optic fibers within the cladding thereby forming an elongate, substantially cylindrical fused fiberoptic rod. The fused fiberoptic rod has an outer diameter less than the predetermined outer diameter of the pre-drawn cladding and is thereafter supported in a vertically-disposed depending position from a rotation device and rotated about its central longitudinal axis. The step of heating the mid-section is accomplished while the fused rod is supported and rotated by the rotation device by a small high temperature flame directed in a transverse direction at the fused rod from a gas fired blow torch. After the fused rod is cut at the stretched and thinned midsection, preferably the probes produced therefrom are bent to form angled distal ends and preferably the ends are cut to size, ground and polished.

According to another aspect of the present invention, a fiberoptic dental light probe is provided. The probe has a light guide body made from a single continuous fused fiberoptic rod having an outer cladding which provides a seal for a bundle of fused optic fibers. The body has an elongate cylindrical proximal end, a distal end having a tapered tip, and an arcuate section interconnecting the proximal and distal ends. The elongate proximal end has a substantially constant diameter throughout its length, and the arcuate section and distal end each have a diameter substantially equal to that of the proximal end except at the tapered tip of the distal end which is reduced in diameter. Preferably, the tapered tip is limited to about a 10 mm length of the distal end and tapers at an angle of about 15° from a central longitudinal axis extending through the distal end. In addition, preferably the diameter of the proximal end, arcuate section, and distal end is about 13 mm except at the tapered tip which tapers to an end surface with a diameter of about 8 mm.

BRIEF DESCRIPTION OF THE DRAWINGS

The foregoing and other objects, features and advantages of the present invention should become apparent from the following description when taken in conjunction with the accompanying drawings, in which.

DETAILED DESCRIPTION OF THE PREFERRED EMBODIMENT

The present invention primarily relates to a method of making a fiberoptic light guide which has a substantially constant diameter along its entire length except within a relatively short length which forms a tapered tip of the light guide. The present invention also relates to the structure and configuration of a light guide made by the method. Therefore, before turning to the details of the method, a description of the details of a specific light guide made in accordance to the present invention is provided.

Figure 1:
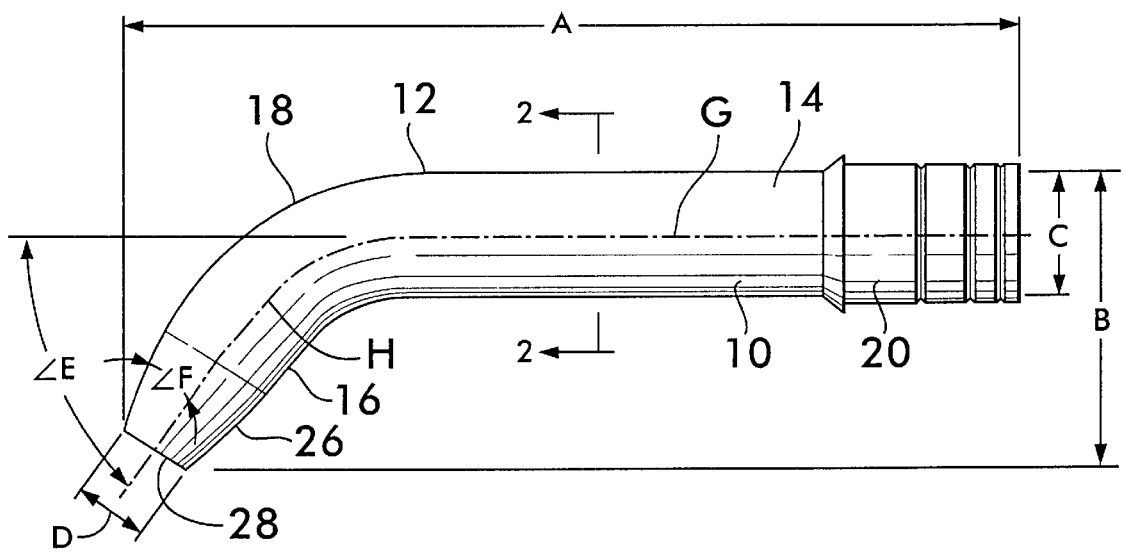
FIG. 1 is a side elevational view of a fiberoptic light probe according to the present invention.
Figure 2:
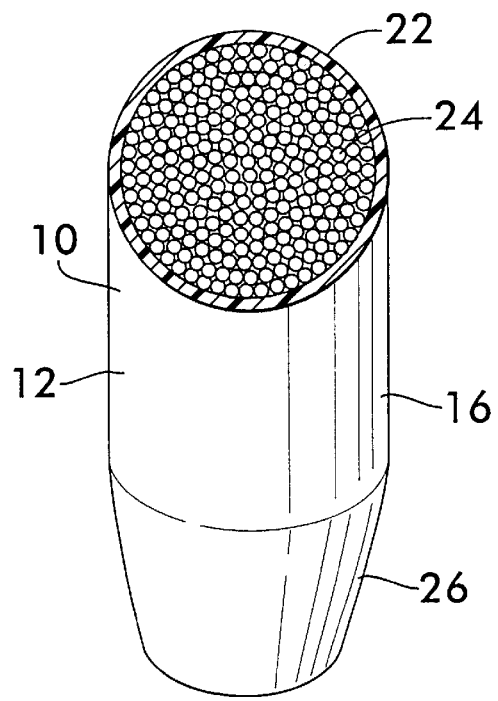
FIG. 2 is a cross-sectional view of the probe illustrated in FIG. 1 along line 2—2.

A light guide 10 is illustrated in FIGS. 1 and 2 and is particularly useful as a dental light probe for use in curing photocurable materials during dental procedures. The light guide 10 has a probe body 12 with an elongate cylindrical proximal end 14 (ie. proximal to the dentist), a relatively short distal end 16, and an arcuate section 18 interconnecting the proximal and distal ends, 14 and 16. The light guide 10 also includes an end fitting 20 which is secured about an end section of the proximal end 14 of the body 12 and which enables the light guide 10 to be readily coupled to a high-intensity light source. Preferably, the end fitting 20 is made of stainless steel and is adhesively secured to the body 12.

As disclosed in U.S. Pat. No. 4,846,546 issued to Joseph Cuda, preferably the body 12 is made of a fused fiberoptic rod having a glass cladding 22. The disclosure provided by the '546 patent is herein incorporated by reference. The use of a fused rod enables a packing fraction of a bundle of optic fibers 24 (see FIG. 2) within the cladding 22 to be over 90% which permits the light guide 10 to transmit considerably more light than a light guide which consists merely of a filled rod (ie. non-fused). In addition, preferably the glass cladding 22 is such that it inhibits the transmission of light transversely through the cladding 22.

As best illustrated in FIG. 1, the body 12 has a substantially constant diameter "C" throughout its proximal end 14, arcuate section 18, and distal end 16 except for a relatively short tapered tip 26 extending from an end surface 28 of the distal end 16. The tip 26 tapers inwardly to the end surface 28 to further concentrate the high intensity light shining through the light guide 10.

By way of example, and not by way of limitation, a preferred body 12 has a diameter "C" (see FIG. 1) of about 13 mm and a tapered tip 26 with an end surface 28 having a diameter "D" (see FIG. 1) of about 8 mm. Of course, other diameter "C"/"D" combinations can be utilized, such as, 12 mm/8 mm, 10 mm/6 mm, 10 mm/4 mm, 8 mm/4 mm and other "C"/"D" combinations. Preferably, the tapered tip 26 extends along an axis "H" (see FIG. 1) through the distal end 16 for about a 10 mm length where it tapers at a straight angle "F" (see FIG. 1) of about 15° relative to axis "H". The length "A" (see FIG. 1) of the light guide 10 is preferably about 3.5 inches with the height "B" (see FIG. 1) of the arcuate section 18 and distal end 16 being about 1.2 inches. In addition, the distal end 16 extends along the axis "H" which, in turn, extends at an angle "E" (see FIG. 1) of about 60° from the longitudinal central axis "G" (see FIG. 1) of the proximal section 14. Further, the fused rod can contain hundreds of optic fibers (see FIG. 2) which each extends continuously between the ends of the light guide 10 within a blue colored glass cladding 22.

DETAILED DESCRIPTION OF THE PREFERRED METHOD

A cylindrical fused fiberoptic rod 30 is utilized to make the light guide 10 according to the present invention. As disclosed in the above referenced '546 patent, the rod 30 is manufactured by inserting a bundle of separate optic fibers within a glass cladding. This assembly is then heated and stretched (ie. "drawn") to heat-fuse the optic fibers together and to seal the optic fibers within the glass cladding. For example, hundreds of optic fibers approximately 1 mm in diameter may be packed into a glass cladding having a diameter of about 40 mm, and this assembly is then drawn to a diameter of about 13 mm. Thus, the diameter of the pre-drawn cladding is substantially greater than the diameter of the fused fiberoptic rod 30. This ensures a high packing fraction and enables the rod 30 to transmit considerably more light than is possible with the pre-drawn assembly.

Figure 3:
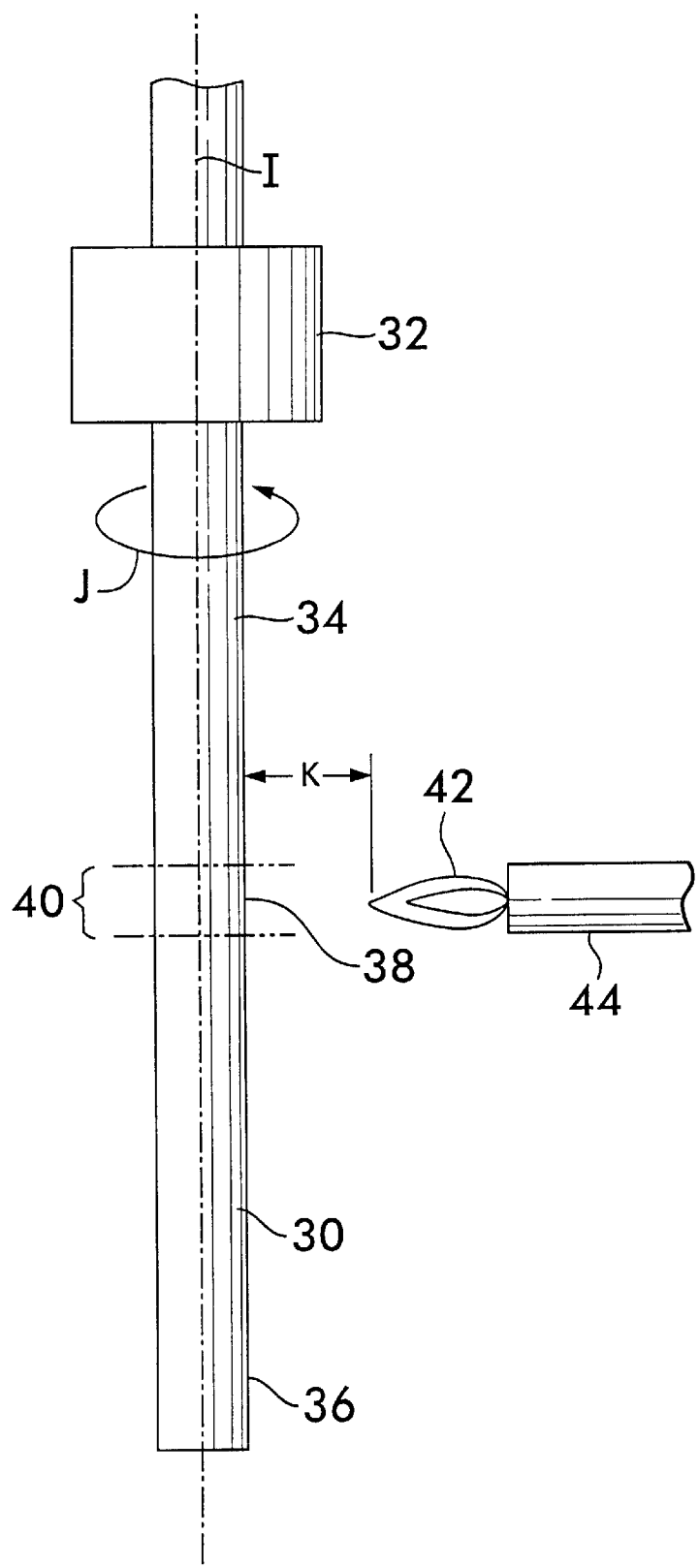
FIG. 3 is a fused fiberoptic rod secured to a rotation device according to the method of the present invention.

The fused fiberoptic rod 30 is cut to a predetermined length and used to make a pair of substantially identical light guides 10 each having a tapered tip 26. As best illustrated in FIG. 3, the rod 30 is preferably supported in a vertically-disposed position from a support device 32. To this end, the rod 30 has opposite ends, 34 and 36, and a mid-section 38 located therebetween, and the upwardly positioned end 34 of the rod 30 is engaged by the support device 32 which is capable of rotating the rod 30 in a direction "J" about its longitudinal central axis "I" as shown in FIG. 3. The purpose of the rotation is to ensure uniform heating, discussed below, of only a localized portion 40 of the mid-section 38.

A small high temperature flame 42 is utilized to heat the localized portion 40 of the mid-section 38. Thus, portion 40 is heated in an open environment, and thereby, the method of the present invention does not require the entire rod to be heated and does not require the placement of the entire rod within a furnace. Preferably, the small flame 42 is provided by a gas-fired blow torch 44 on a small flame setting, and the flame 42 is positioned about two to three inches (see dimension "K" in FIG. 3) from portion 40 of the rod 30 in a direction substantially perpendicular to the axis "I" of the rod 30. Thus, the present invention provides the advantage of eliminating the need for expensive furnace equipment and instead utilizes relatively inexpensive gas-fired blow torches to provide a heat source.

Figure 4:
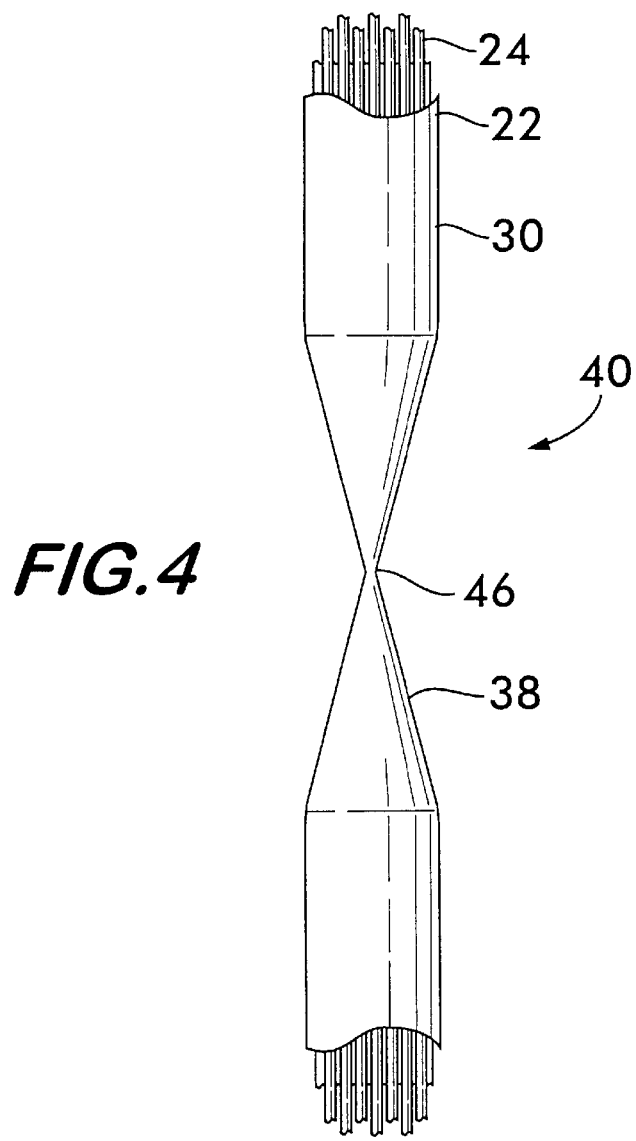
FIG. 4 is the fused fiberoptic rod illustrated in FIG. 3 after its mid-section has been heated, softened, and then permitted to stretch under the force of gravity.
Figure 5:
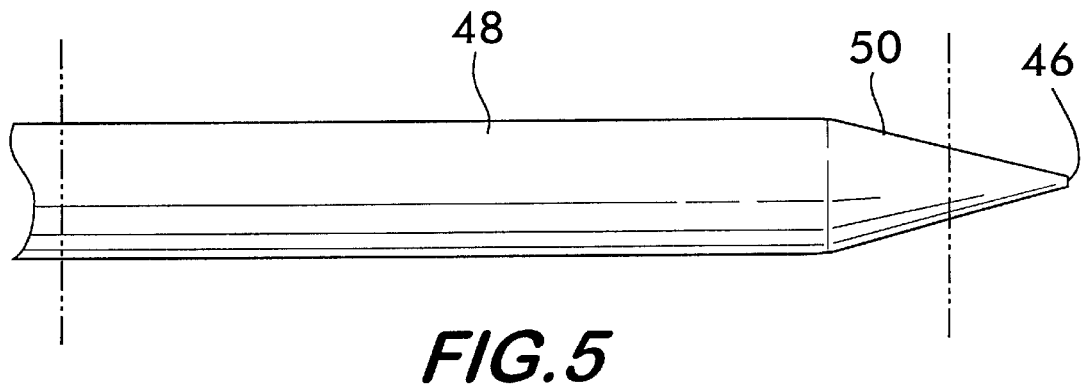
FIG. 5 is one of the pair of tapered tip probes produced by cutting the midsection of the fused fiberoptic rod illustrated in FIG. 4.

As the rod 30 is rotated, the single flame 42 evenly heats portion 40 of rod 30 to soften portion 40. This is the only portion of the rod 30 that is subject to heat; thus, the remaining sections of the rod 30 are not modified during the heating step. The weight of the lowermost end 36 of the rod 30 causes the softened portion 40 to stretch (ie., elongate) solely by the force of gravity. The stretching of portion 40 causes portion 40 to thin and form a substantially hourglass shape as illustrated in FIG. 4. The heat source is removed from portion 40 when the rod lengthens to a predetermined set point at which time the thinnest section 46 of portion 40 has a diameter of only slightly more than 1 mm. After the heat is removed, the rod 30 discontinues stretching and is permitted to cool to ambient. Thereafter, the rod 30 is cut at the thinnest section 46 of portion 40 preferably with carbide scissors to form a pair of substantially identical light guides 48 each having a tapered tip 50 (see FIG. 5).

The ends of each light guide 48 is cut with a diamond jig to form a light guide of a desired length and to form the desired sized end surface of the tapered tip of the light guide. For instance, the tapered tip 48 can be cut so that the end surface of the tapered tip 48 has a diameter of 8 mm. In addition, the jig is utilized to grind and polish the newly cut ends of the light guide to ensure maximized light transmission therethrough.

Further, the end of the light guide having the tapered tip can be heated and bent to form an arcuate section so that the distal end of the light guide is angled relative to the proximal end. An end fitting can be secured to the proximal end of the light guide so that the light guide can be readily coupled to a high-intensity light source.

The above referenced method enables fiberoptic light probes to be manufactured in a cost efficient manner requiring only a minimum of equipment and skill. The light guide 10 produced thereby can have a substantially constant diameter throughout its length except in a relatively short length where a tapered tip is provided to concentrate light to the end surface of the distal end of the light guide. To this end, the taper angle "F" (see FIG. 1) of the tapered end of the light guide can be about 15° and can extend from a diameter of about 13 mm to a diameter of about 8 mm within about a 10 mm length.

While a preferred method and light guide have been described in detail, various modifications, alterations, and changes may be made without departing from the spirit and scope of the method and light guide according to the present invention as defined in the appended claims.

What is claimed is:

1. A method of making a fiberoptic light guide, comprising the steps of:

supporting an elongate fused fiberoptic rod in a vertically disposed position, said elongate rod having opposite ends and a midsection located therebetween;

heating only said mid-section of said elongate fused fiberoptic rod to soften said mid-section such that said mid-section elongates under the force of gravity;

discontinuing said heating step when said fused rod elongates to a predetermined set point to prevent said mid-section from further stretching and to permit said mid-section to cool; and after said mid-section cools, cutting said elongate fused fiberoptic rod at said stretched mid-section to provide a pair of fiberoptic light guides with tapered tips.

2. A method according to claim 1, wherein, before said heating step, said elongate fused fiberoptic rod is cylindrical and has a substantially constant diameter throughout its length, and wherein each of said pair of fiberoptic light guides formed form said elongate fused rod has a diameter substantially identical to said diameter of said fused rod except at said tapered tips which have reduced diameters.

3. A method according to claim 1, wherein a gas fired torch providing a small high temperature flame is directed in a transverse direction at said fused rod during said heating step to heat only a small localized section of said fused rod so that stretching of said fused rod is confined to said small localized section which forms said tapered tips and so that softening and stretching of any other part of said fused rod is prevented.

4. A method according to claim 3, further comprising the step of rotating said fused fiberoptic rod about its central longitudinal axis during said heating step so that said small localized section of said fused rod is heated evenly by said small flame.

5. A method according to claim 4, wherein, during said heating step, said small flame is spaced about 2 to 3 inches from said fused rod in a direction perpendicular to said central longitudinal axis of said fused rod.

6. A method according to claim 1, wherein said set point is reached when a portion of said mid-section reduces in diameter to about 0.05 inch.

7. A method according to claim 1, further comprising the steps of: cutting both ends of one of said formed light guides to provide said light guide with a desired length and to provide said tapered tip with a desired end surface; and bending said formed light guide adjacent said tapered tip to provide a light guide having a bent distal end.

8. A method according to claim 7, wherein said formed light guide has a substantially constant diameter within a range of about 13 to 8 mm from a proximal end thereof through said bent distal end except at said tapered tip in which said end surface has a diameter within a range of about 8 to 4 mm.

9. A method according to claim 8, wherein said tapered tip is limited to about 10 mm in length.

10. A method according to claim 7, further comprising the steps of: grinding and polishing both of said cut ends of said formed light guide after said bending step; and securing an end fitting to said end of said formed light guide opposite said bent distal end.

11. A method according to claim 1, wherein said tapered tip is formed such that it tapers at an angle of about 15° from said central longitudinal axis of said fused rod.

12. A method of making a fiberoptic dental light probe including the steps of: inserting a bundle of optic fibers into a glass cladding having a predetermined outer diameter; heating said cladding and optic fibers; and drawing said cladding and optic fibers to fuse said bundle of optic fibers together and to seal said bundle of optic fibers within said cladding thereby forming an elongate fused fiberoptic rod; said fused fiberoptic rod having an outer diameter less than said predetermined outer diameter of said glass cladding; wherein the improvement comprising the steps of:

supporting said elongate fused fiberoptic rod in a vertically-disposed depending position from a rotation device and rotating said fused fiberoptic rod about its central longitudinal axis, said elongate rod having opposite ends and a mid-section located therebetween;

while said fused rod is being supported and rotated by said rotation device, heating only said mid-section of said elongate fused fiberoptic rod with a small high temperature flame directed in a transverse direction at said fused rod from a gas fired torch to soften said mid-section to an extent that said mid-section is caused to stretch and elongate under the force of gravity;

discontinuing said heating step when said fused rod elongates to a predetermined set point to prevent said mid-section from further stretching and to permit said mid-section to cool; and after said mid-section cools, cutting said elongate fused fiberoptic rod at said stretched mid-section to provide a pair of fiberoptic light probes with tapered tips.

13. A method according to claim 12, wherein, during said heating step, said small flame is spaced about 2 to 3 inches from said fused rod in a direction perpendicular to said central longitudinal axis of said fused rod.

14. A method according to claim 12, wherein when said set point is reached, a most reduced portion of said stretched mid-section reduces in diameter to about 0.05 inch.

15. A method according to claim 12, further comprising the steps of: cutting both ends of one of said formed light probes to provide said light probe with a desired length and to provide said tapered tip with a desired end surface; and bending said formed light probe adjacent said tapered tip to provide a light guide having a bent distal end.

16. A method according to claim 15, further comprising the steps of: grinding and polishing both of said cut ends of said formed light probe after said bending step; and securing an end fitting to said end of said formed light probe opposite said bent distal end.

* * * * *